US012667403B2

(12) United States Patent
Gillies

(10) Patent No.: US 12,667,403 B2
(45) Date of Patent: Jun. 30, 2026

(54) ORTHOPAEDIC REDRESSING DEVICE

(71) Applicant: Medical Device Research Australia Pty Ltd, Enmore (AU)

(72) Inventor: Ronald Mark Gillies, Enmore (AU)

( * ) Notice: Subject to any disclaimer, the term of this patent is extended or adjusted under 35 U.S.C. 154(b) by 105 days.

(21) Appl. No.: 18/832,097

(22) PCT Filed: Jan. 21, 2022

(86) PCT No.: PCT/AU2022/050026
§ 371 (c)(1),
(2) Date: Oct. 23, 2024

(87) PCT Pub. No.: WO2022/155707
PCT Pub. Date: Jul. 28, 2022

(65) Prior Publication Data
US 2025/0143765 A1 May 8, 2025

(30) Foreign Application Priority Data

Jan. 21, 2021 (AU) ................................. 2021900134

(51) Int. Cl.
*A61B 17/88* (2006.01)
*A61F 2/30* (2006.01)

(52) U.S. Cl.
CPC ............ *A61B 17/8863* (2013.01); *A61F 2/30* (2013.01); *A61F 2002/30332* (2013.01)

(58) Field of Classification Search
CPC .... B24D 5/10; B24D 5/02; A61F 2/30; A61B 17/88; A61B 17/8863
See application file for complete search history.

(56) References Cited

U.S. PATENT DOCUMENTS

| | | | |
|---|---|---|---|
| 3,020,787 A | 2/1962 | Cusick | |
| 5,564,871 A | 10/1996 | Lagsdin | |
| 11,331,133 B2 * | 5/2022 | Gillies | ............... A61B 17/8863 |
| 2008/0103500 A1 * | 5/2008 | Chao | .................. A61B 17/8863 |
| | | | 606/84 |
| 2010/0111631 A1 | 5/2010 | Trieu | |
| 2019/0151004 A1 * | 5/2019 | Gillies | ............... A61B 17/8863 |

FOREIGN PATENT DOCUMENTS

DE       202006018176 U1    3/2007

* cited by examiner

Primary Examiner — Christopher J Beccia
(74) *Attorney, Agent, or Firm* — Assouline & Berlowe, PA; Peter A. Koziol, Esq.

(57) ABSTRACT

The present disclosure is directed to a device for redressing a tapered portion of an orthopaedic implant. The device comprises a grinding member adapted to matingly contact or engage at least a portion of the tapered portion; a housing adapted for removably receiving the grinding member therein, the housing having an opening at or towards a distal end to receive the tapered portion therethrough; and a connector at or towards a proximal end for operably connecting the housing to a drill member.

12 Claims, 4 Drawing Sheets

SECTION J-J

SECTION H-H

ORTHOPAEDIC REDRESSING DEVICE

FIELD

This invention relates to an orthopaedic redressing device. More specifically, it relates to a device for redressing a tapered portion of an orthopaedic implant.

BACKGROUND

Modular taper (or trunnion) junctions are a common element in current total joint replacement design. The use of the taper junction is to allow the surgeon the ability to interoperatively adjust/modify the joint replacement implant to better fit the patient during surgery. In total joint arthroplasty this modularity allows for a better intraoperative restoration of joint stability via the ability to select and use different femoral or humeral head bearing material types (e.g., metal or ceramic) and sizes (e.g., various head diameters and offsets). Modular taper junctions are also used in the knee joint and typically used with revision knee systems where an intermedullary rod is used to support the femoral and/or tibial components. The use of femoral or humeral heads on taper junctions, however, can inevitably lead to micro-motion occurring between the head and its associated taper. The magnitude of this micro-motion will depend on the size of the head used and also the mismatch between the male and female taper angles.

A clinical problem that has become apparent in recent years is the disease commonly referred to as "trunnionosis". Clinically, trunnionosis is defined as the wear of the femoral head-neck interface, due to micro-motion, and has been acknowledged as a source of total hip arthroplasty (THA) failure. The etiology of clinically relevant trunnion corrosion appears to be multifactorial with synergy among implant-based, surgeon-based, and patient-based factors.

This phenomenon appears to have gained prevalence with newer THA implant designs, in particular metal-on-metal prostheses. Whilst modularity enables a more customised fit for the patient, it may have untoward effects. By way of example, this modularity at times may play a role in increased wear and mechanical insufficiency at the taper, ultimately leading to revision. Trunnionosis is estimated to account for up to 3% of all THA revision procedures. The exact cause of trunnionosis currently remains poorly understood, but contributing factors may include wear between metal-on-metal modular junctions, corrosion and fretting damage, and the release of metal ions or particulate debris from affected components. Additionally, varying implant designs and geometries may have, in some cases, demonstrated a predisposition to excessive fretting and corrosion of the trunnion leading to failure. [1-4]

The generally accepted solution to trunnionosis is revision surgery which represents a costly and risky procedure with a decreased chance of positive outcomes, as blood loss and bone stock is generally compromised. It is not uncommon, however, that if the femoral stem is well fixed it will be left in place and only the metal femoral head may be replaced, such that a new femoral head may be placed onto the damaged male taper. This clearly introduces compromises with respect to the implant, as the original taper was likely highly controlled in terms of its dimensions/tolerances and surface finish. Accordingly, following replacement of the femoral head the implant may be more susceptible to subsequent failure.

Another surgical situation that requires the removal of the femoral head occurs when the acetabular liner requires replacement due to either wear or failure. The surgical procedure will require the femoral head the be removed in order to facilitate the insertion of the new acetabular liner. The femoral head will also need to be replaced. Again, following replacement of the femoral head the implant may be more susceptible to subsequent failure.

Therefore, an alternative or improved approach to the treatment of trunnionosis, or the like, that reduces the risk of subsequent implant failure is required.

SUMMARY OF INVENTION

The present invention is broadly directed to a redressing device or tool for redressing a tapered portion of an orthopaedic implant. It would be readily apparent that the redressing device may be used on any orthopaedic implant known in the art that includes a tapered portion, including male tapered portions. In this regard, such tapered portions are generally present in many types of orthopaedic implants, such as hip, knee and shoulder joint replacement implants. The invention is further directed to a method of redressing a tapered portion of an orthopaedic implant that includes use of the device described herein.

In a first aspect, the invention provides a device for redressing a tapered portion of an orthopaedic implant comprising:

a grinding member adapted to matingly contact or engage at least a portion of the tapered portion;

a housing adapted for removably receiving the grinding member therein, the housing having an opening at or towards a distal end to receive the tapered portion therethrough; and a connector at or towards a proximal end for operably connecting the housing to a drill member.

Suitably, the grinding member comprises first and second portions that are separable from each other. In particular embodiments, the first and second portions are separable along an axis, such as a longitudinal axis, thereof. Preferably, the first and second portions are of substantially equal dimensions.

Suitably, the grinding member comprises a tapered aperture or recess to facilitate contact or engagement of the tapered portion with an inner grinding surface therein. In certain embodiments, the inner grinding surface is or comprises a diamond coating. In some embodiments, the inner grinding surface has a Rz value of between about 5 microns (i.e. 5 $\mu$m) to about 25 microns (i.e. 25 $\mu$m) and more particularly about 8 microns (i.e. 8 $\mu$m) to about 20 microns (i.e. 20 $\mu$m).

In various embodiments, the tapered aperture or recess is substantially frustoconical in shape.

In particular embodiments, the housing comprises a recessed portion for removably receiving the grinding member therein.

In some embodiments, the recessed portion and the grinding member are substantially frustoconical in shape. In this regard, the grinding member and the recessed portion suitably taper from the distal end to the proximal end.

Suitably, the housing further includes a cap disposed at or towards a distal end thereof, the cap comprising the opening and configured for reversibly closing the housing and retaining the grinding member therein. In some embodiments, the cap includes an annular lip disposed at or towards the distal end thereof and extends inwardly therefrom so as to define the opening of the housing therebetween.

In certain embodiments, the housing includes one or more apertures that extend through an outer wall thereof into the recess. In particular embodiments, the one or more apertures extend into a base portion of the recess. In some embodiments, the housing includes first and second apertures disposed at opposing sides of the housing. Suitably, the first and second apertures are parallel and planarly offset relative to each other.

Suitably, the housing includes a cylindrical portion at the distal end and a tapered portion extending proximally from the cylindrical portion to the connector.

In a second aspect, the invention resides in a kit comprising the device of any one of the first aspect and a drill member.

In a third aspect, the invention relates to a method of redressing a tapered portion of an orthopaedic implant including the steps of:

(i) providing a device comprising: a grinding member adapted to matingly contact or engage at least a portion of the tapered portion; a housing adapted for removably receiving the grinding member therein, the housing having an opening at or towards a distal end to receive the tapered portion therethrough; and a connector at or towards a proximal end for operably connecting the housing to a drill member;

(ii) contacting or engaging the device with the tapered portion; and (iii) redressing the tapered portion with the device.

Suitably, the device is that of the first aspect.

BRIEF DESCRIPTION OF DRAWINGS

In order that the present invention may be readily understood and put into practical effect, reference will now be made to the accompanying illustrations, wherein like reference numerals are used to refer to like elements.

DESCRIPTION OF EMBODIMENTS

FIGS. 1 through 7 demonstrate an embodiment of a device for redressing a tapered portion, such as a male configuration thereof, of an orthopaedic implant. It would be appreciated that this device is suitably for redressing a damaged tapered portion, preferably interoperatively, so as to facilitate engagement of a corresponding component, such as a new femoral head component, thereon and thereby maximize the contact area between the respective male and female tapered portions.

As would be appreciated by the skilled artisan, hip replacement components typically include an elongated femoral stem component, which is typically metallic and has a lower end to fit endwise into a corresponding recess formed in a femur and a neck portion that extends generally angularly from the upper end of the femoral stem component. An upper end portion of the femoral stem component typically includes a tapered portion, such as a tapered recess/bore or a tapered extension/nose (i.e., a trunnion), adapted to receive a corresponding tapered extension/nose or recess/bore respectively in a femoral head component of the orthopaedic implant. The femoral head component is generally metallic or ceramic and is of suitable dimensions to be received into a socket defined by the joint of interest.

When installed on the femoral stem component, the femoral head component is positioned to bear on either the patient's natural acetabulum or an acetabular component which has been implanted into the patient's pelvis to replace his or her acetabulum. In such a manner, the orthopaedic implant and the natural or artificial acetabulum collectively function as a system which replaces the natural joint of the patient's hip. To this end, the acetabular component may include an acetabular shell which comprises a tapered recess into which an acetabular liner of suitable dimensions typically matingly engages.

Figure 1:
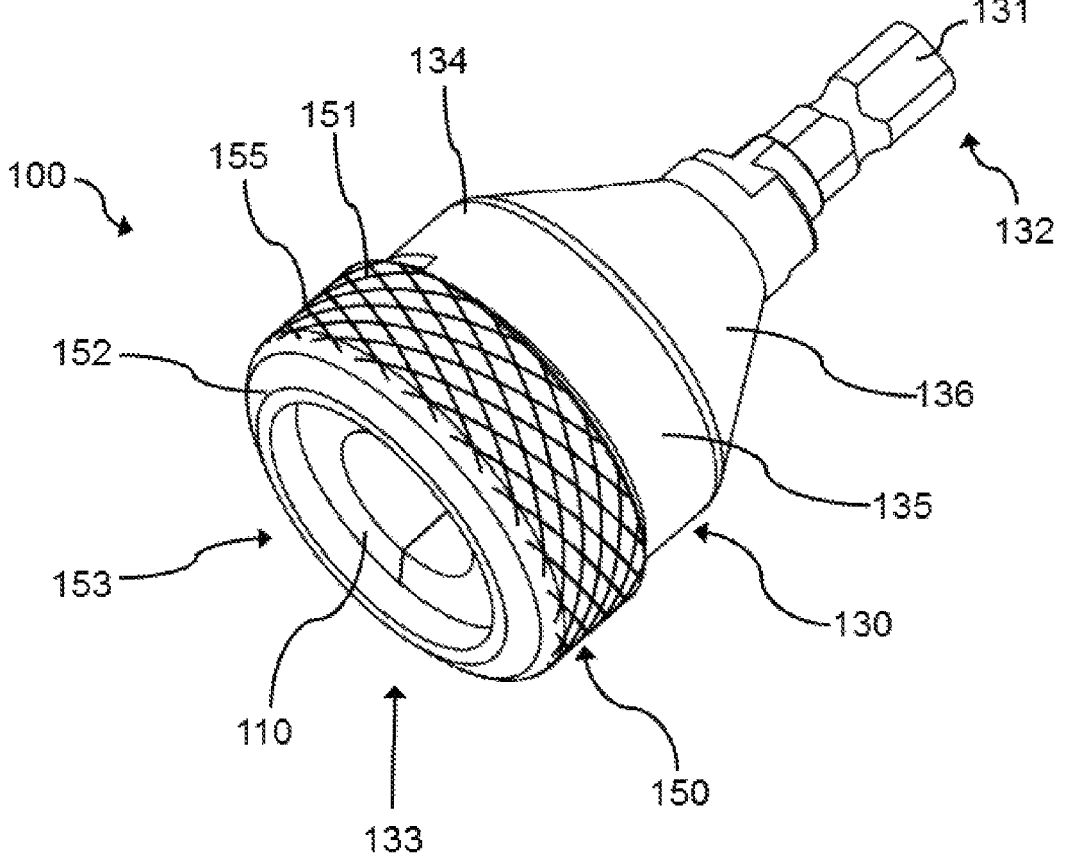
FIG. 1 is a perspective view of an embodiment of a device of the invention.

In FIG. 1, the modular device 100 suitably includes a grinding member 110, a housing 130 for receiving the grinding member 110 therein and a cap or lid 150 for closing the housing 130.

Figure 2:
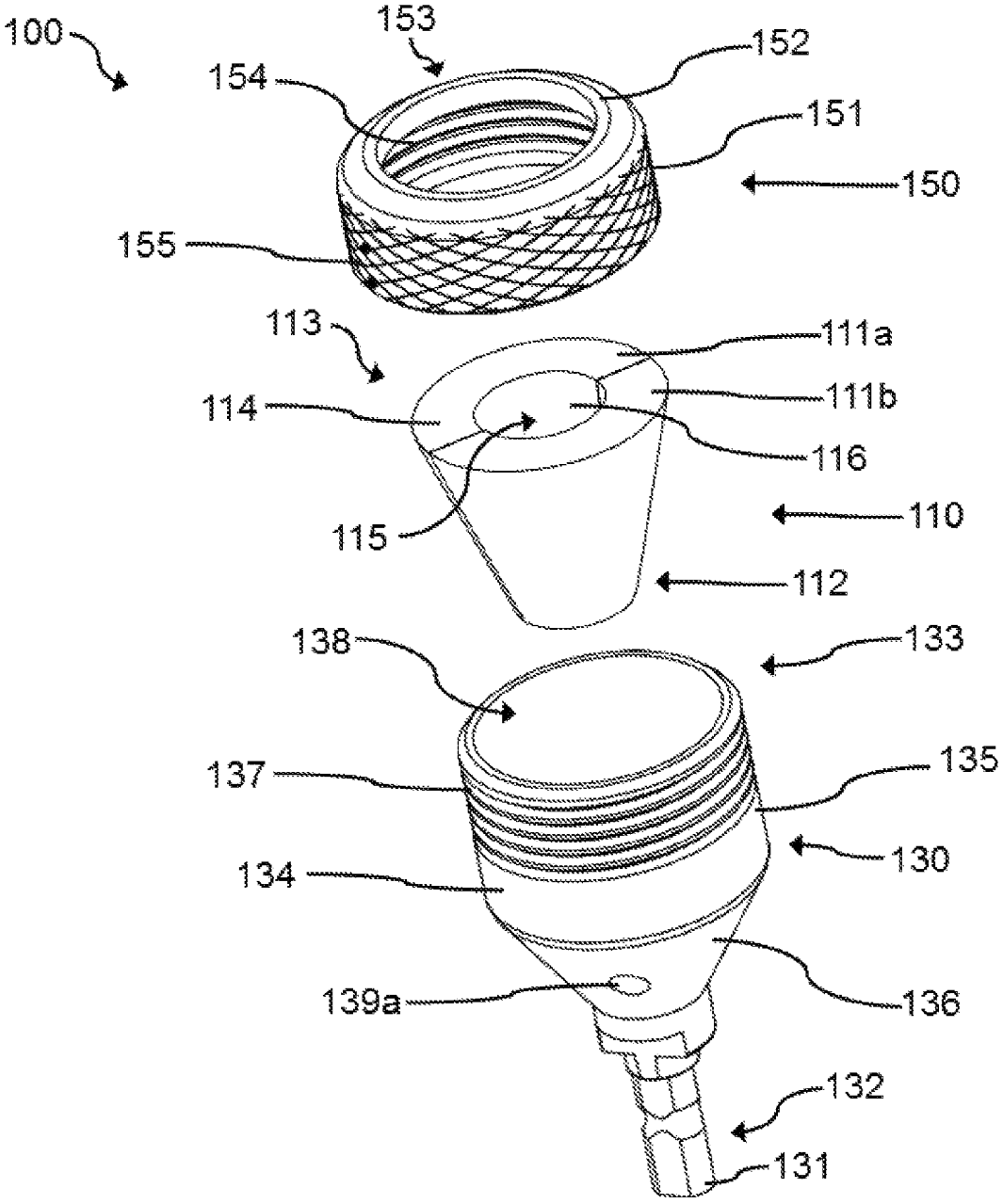
FIG. 2 is an exploded view of the device of FIG. 1.
Figure 6:
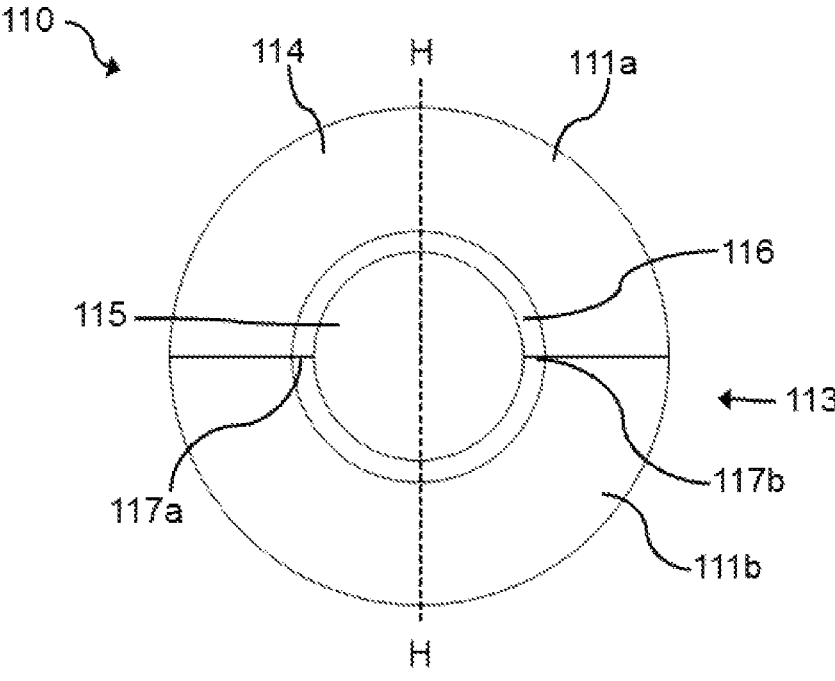
FIG. 6 is a front end view of a grinding member of the device of FIG. 1.
Figure 7:
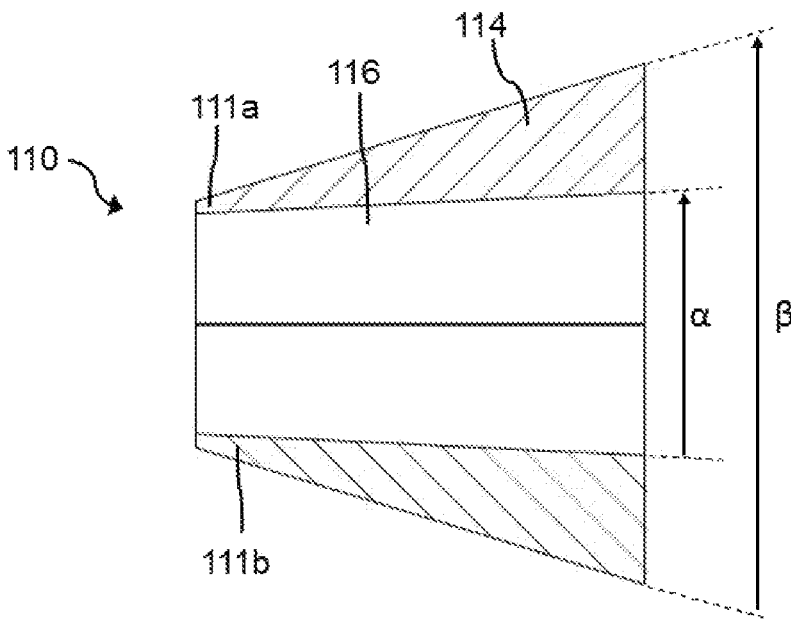
FIG. 7 is a central longitudinal cross section through the plane H-H of FIG. 6 of the device of FIG. 1.

As illustrated in FIGS. 2, 6 and 7, the grinding member 110 comprises first and second grinding elements or portions 111a,b that are separable from each other longitudinally so as to comprise two equally dimensioned semi-annular portions. This modular arrangement advantageously allows for a grinding surface of the first and second grinding portions 111a,b to be coated evenly, such as with a diamond coating, during the manufacturing process. The skilled person would appreciate that it is important that the "roundness" of the taper is maintained during redressing by the device 100 and that this can be more readily achieved through having the arrangement of first and second grinding portions 111a,b that are coated individually, as hereinafter described. Additionally, in some embodiments, inner edges 117a,b that extend longitudinally on each opposing side of the grinding portions 111a,b are rounded or chamfered (e.g., have a radius of about 0.1 mm to about 0.4 mm (e.g., about 0.1, 0.15, 0.2, 0.25, 0.3, 0.35, 0.4 mm and any range therein)). In one particular embodiment not shown in the figures, each of the grinding portions 111a,b include a chamfer that defines a notched or stepped arrangement or profile (e.g., about 0.05 mm to about 0.2 mm in length and about 0.05 mm to about 0.15 mm in width) at the inner edges 117a,b thereof and extending therealong from the proximal end 112 to the distal end 113 with the innermost edge thereof suitably being rounded. The semicircular inner edge portions at respective proximal and distal ends 112,113 of each of the grinding portions 111a,b may also be rounded or chamfered (e.g., have a radius of about 0.1 mm to about 0.4 mm) as required.

It is envisaged, however, that the grinding member 110 may alternatively be of unitary structure or be comprised of more than two (e.g., 3, 4, 5, 6 etc) individual grinding elements or portions. When suitably positioned together, the first and second grinding portions 111a,b include an annular body wall 114 that defines a frustoconical shape of the outer surface of the grinding member 110 and a tapered aperture 115 therewithin that opens at respective proximal and distal ends 112,113 thereof. It will be appreciated that alternative shapes to the grinding member 110, such as cuboidal and the like, are also to be encompassed by the present invention.

The first and second grinding portions 111a,b of the grinding member 110 further include or define an inner grinding surface 116 and a space or grinding zone therebetween. In the embodiment provided, the inner grinding surface 116 and the corresponding tapered aperture 115 are substantially frustoconical in shape (i.e., taper or decline in width from the distal end 113 to the proximal end 112 thereof) so as to matingly receive and contact a substantially frustoconical tapered portion of an orthopaedic implant, such as a femoral stem component (not shown), therein. In various embodiments, the width or diameter of the tapered aperture 115 is: (a) between about 7 mm and about 15 mm (e.g., about 7, 7.5, 8, 8.5, 9, 9.5, 10, 10.5, 11, 11.5, 12, 12.5, 13, 13.5, 14, 14.5, 15 mm and any range therein), and more particularly between about 11 mm to about 13 mm, at or towards a distal end of the grinding member 110; and/or (b) between about 5 mm to about 20 mm (e.g., about 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20 mm and any range therein), and more particularly between about 12 mm to about 15 mm, at or towards a proximal end of the grinding member 110.

To assist in maintaining or ensuring consistency in dimensions of the inner grinding surface 116 between the first and second grinding portions 111*a,b*, (and hence assist in maintaining the "roundness" of the taper during redressing thereby), the respective grinding portions 111*a,b* may be welded or joined together along their long axis and then the tapered aperture 115 can be machined therein simultaneously rather than separately for each individual grinding portion 111*a,b*.

Based on the above, it will be understood by the skilled artisan that the shape and/or dimensions of the inner grinding surface 116 may be adapted for the present invention so as to substantially match or correspond to the shape of the tapered portion of the orthopaedic implant as required. Additionally, given the ability of the grinding member 110 to be removed from the housing 130, a user may select a specific grinding member 110 from a selection having different shapes, sizes, angles, roughnesses and/or configurations of their inner grinding surfaces 116 as is appropriate for, for example, the size of the tapered portion to be redressed and/or the degree of redressing required. Accordingly, the device 100 advantageously allows for use of a single housing 130 and cap 150 with a range of different grinding members 110 that may be suitable for redressing the tapered portion of a variety of different orthopaedic implants and hence be used interchangeably by a user as required.

Suitably, at least a portion of the inner grinding surface 116 is configured to be of a specific roughness (e.g., an Ra or Rz value), such as by a diamond coating (or other suitable coating known in the art) or roughening the surface thereof. In particular embodiments, the inner grinding surface 116 has an Rz value of between about 5 microns to about 25 microns (e.g., about 5, 6, 7, 8, 9, 10, 11, 12, 13, 14, 15, 16, 17, 18, 19, 20, 21, 22, 23, 24, 25 microns and any range therein) and more particularly about 8 microns to about 20 microns.

As shown in FIG. 7, the inner grinding surface 116 of the grinding member 110 has a inner taper angle $\alpha$ and an inner taper diameter that substantially match an implant taper angle and an implant taper diameter along the length of a tapered portion of an orthopaedic implant (not shown). It will be appreciated by the skilled artisan, that each orthopaedic implant's tapered portion may vary depending, for example, on the size of the femoral stem component and/or femoral head component (not shown) to be used. Typically, however, the tapered portion of the femoral stem component and the corresponding tapered portion of the femoral head component (not shown) are commonly sized across the range of component sizes, such that each of the differently-sized head components is generally compatible with each of the differently-sized femoral stem components. Accordingly, in particular embodiments, the first taper angle $\alpha$ is between about 1° to about 10° (e.g., about 1°, 1.5°, 2°, 2.5°, 3°, 3.5°, 4°, 4.5°, 5°, 5.5°, 6°, 6.5°, 7°, 7.5°, 8°, 8.5°, 9°, 9.5°, 10° and any range therein), more particularly between about 3° to about 8°, even more particularly between about 4° to about 7° and yet even more particularly between about 5° to about 6°.

The outer surface of the grinding member 110 further defines an outer taper angle $\beta$ thereof. In the embodiment shown in FIG. 7, the outer taper angle $\beta$ is greater than the first taper angle $\alpha$ such that the annular body wall 114 of the grinding member 110 thins or tapers in cross-section from a distal end 113 to a proximal end 112 thereof. In particular embodiments, the outer taper angle $\beta$ is in the range of about 5° to about 50° (e.g., about 5°, 5.5°, 6°, 6.5°, 7°, 7.5°, 8°, 8.5°, 9°, 9.5°, 10°, 10.5, 11°, 11.5°, 12°, 12.5°, 13°, 13.5°, 14°, 14.5°, 15°, 15.5°, 16°, 16.5°, 17°, 17.5°, 18°, 18.5°, 19°, 19.5°, 20°, 20.5°, 21°, 21.5°, 22°, 22.5°, 23°, 23.5°, 24°, 24.5°, 25°, 26°, 26.5°, 27°, 27.5°, 28°, 28.5°, 29°, 29.5°, 30°, 30.5°, 31°, 31.5°, 32°, 32.5°, 33°, 33.5°, 34°, 34.5°, 35° and any range therein) and more particularly between about 30° to about 40°.

With reference to the device of FIG. 1, a centrally located attachment shaft 131 extends outwardly and axially from a proximal end 132 of the housing 130. In the embodiment provided, the attachment shaft 131 is a detachable zimmer fitting and, as such, is adapted to be reversibly and operably attached or coupled to, for example, an orthopaedic surgical drill (not shown). It will be understood, however, that alternative means of functionally attaching the device 100 to a surgical drill or the like, as are known in the art, may be utilized for the present invention. By way of example, the connection may be a chuck or the like, a proprietary connection, or a male-female connection as are known in the art. Once the attachment shaft 131 or other connector is operably connected to a motor or surgical drill, the device 100 (and hence the grinding member 110 contained therein) can then be rotationally driven thereby about a longitudinal axis of the device 100 as required by a user.

Figure 3:
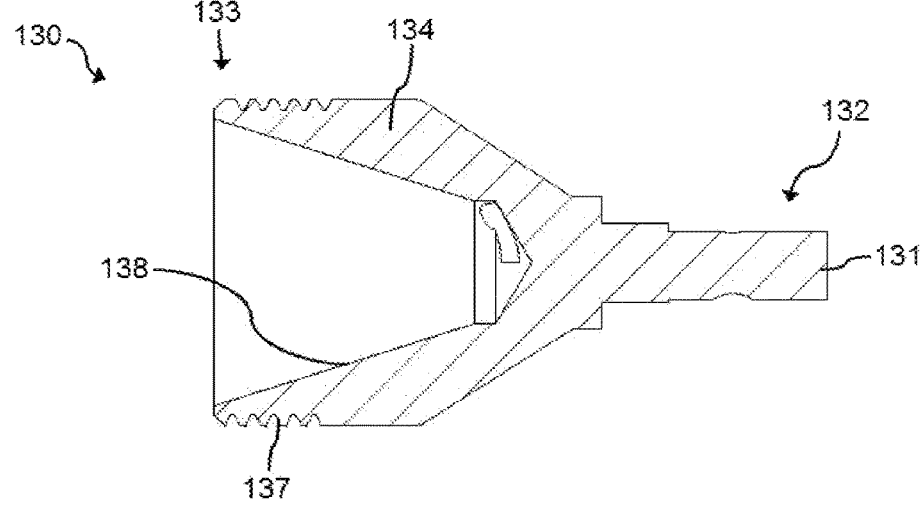
FIG. 3 is a central longitudinal cross section view of a housing of the device of FIG. 1.
Figure 4:
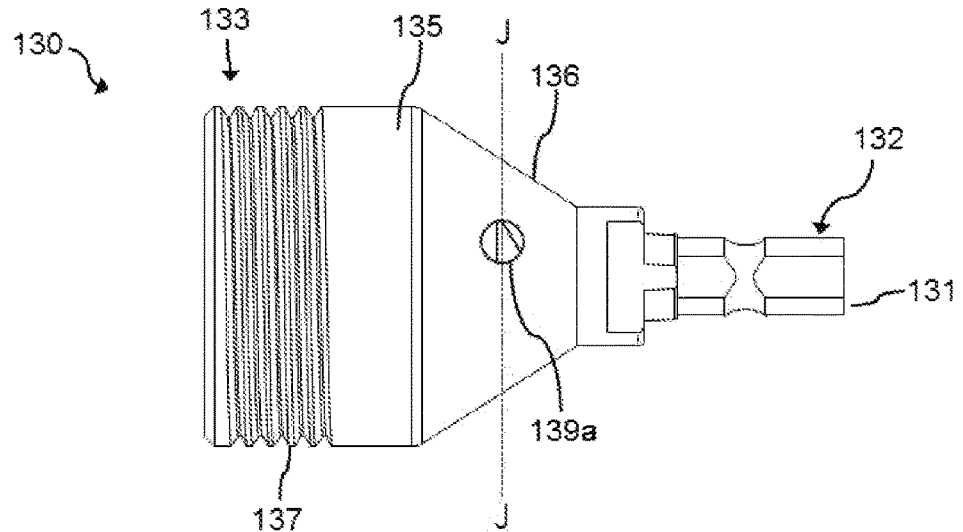
FIG. 4 is a side view of the housing of the device of FIG. 1.
Figure 5:
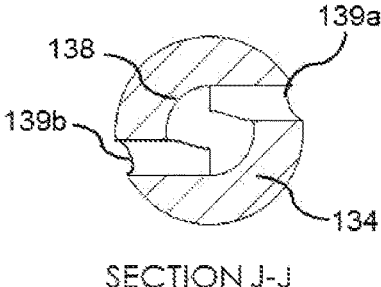
FIG. 5 is a cross section view through the plane J-J of FIG. 4 of the device of FIG. 1.

As can be observed from FIGS. 3 and 4, the housing 130 includes an outer wall 134 having a cylindrical portion 135 that defines a distal end of the housing 130 and a tapered or inclined portion 136 extending proximally therefrom to the base of the attachment shaft 131. The cylindrical portion 135 of the housing 130 further includes an outer threaded section 137 disposed at an outer surface of the distal end thereof. The outer wall 134 of the housing 130 also defines a frustoconical or conical recess 138 that opens axially at or towards a distal end 133 thereof. Suitably, the frustoconical recess 138 is of suitable dimensions and/or configuration so as to matingly receive the grinding member 110 therein when in use.

In particular embodiments, the housing 130 further includes one or more channels or apertures that extend through the outer wall thereof into the frustoconical recess. As can be seen in the embodiment in FIGS. 2 and 4, the housing 130 of device 100 includes a pair of apertures 139*a,b* that extend through the outer wall 134 of the inclined portion 136 into a base or bottom portion of the frustoconical recess 138. From FIG. 5, the pair of apertures 139*a,b* are disposed in respective opposite sides of the housing 130 and planarly parallel and offset to each other relative to a central axis and the longitudinal axis of the housing 130. It is envisaged, however, that a single aperture or more than two apertures (e.g., 3, 4, 5 etc) may be successfully utilized for the present invention. The apertures 139*a,b* are designed to promote drainage and removal of any fluids and/or solid materials or debris produced as a result of a taper redressing procedure that may collect in the base portion of the frustoconical recess 138. Additionally, the apertures 139*a,b* allow a cooling fluid, such as saline, to flow or circulate through and over the grinding member 110 during use so as to assist in cooling the device 100 and remove ground debris therefrom.

As can be observed from FIGS. 1 and 2, the device 100 further includes the cap 150 for securing and retaining the grinding member 110 in the housing 130 once inserted therein. The cap 150 has a domed shape with a hollow cylindrical body 151 and an annular lip 152. The annular lip 152 extends inwardly from a distal end of the cylindrical body 151, so as to define a central opening 153 therebetween for receiving the tapered portion of the orthopaedic implant (not shown) therethrough. The annular lip 152 is further configured to abut or overlie the distal end 113 of the grinding member 110 when appropriately engaged with the housing 130. In this manner, the annular lip 152 maintains the grinding member's 110 position within the frustoconical recess 138 of the housing 130 during use. To this end, the cap 150 further includes an inner threaded section 154 disposed on an inner surface of the cylindrical body 151 that is configured for matingly and threadingly or screwingly engaging the outer threaded section 137 of the housing 130. An outer surface of the cylindrical body 151 further includes cross-hatched indentations 155 extending substantially therearound so as to assist a user in gripping the cap 150 during removal from the housing 130.

Although the cap 150 of device 100 is removable from the housing 130, alternative embodiments in which the cap 150 is not removable or fixed to the housing, such as by way of a flexible tab or connection, are also envisaged for the present invention. It is further envisaged that further structural elements in addition to the cap 150 can be utilized to maintain the rotational stability of the grinding member 110 within the housing 130, such as corresponding interlocking elements therebetween, when in use.

With respect to the embodiment provided herein, it will be appreciated that the rotational speed and/or the direction of rotation of the device 100, and hence the grinding member 110 therein, are preferably variable, such as by employing a reversible motor or a surgical drill including a reversible motor. Such an arrangement may assist in regulating, for example, the amount of fretting and/or corrosion removed from the contact surfaces of the tapered portion of the orthopaedic implant during use of the device 100. It would also be apparent that in addition or alternatively to rotational movement, the grinding member 110 may also be configured to perform axial movement, or the like, relative to a longitudinal axis thereof.

In this specification, adjectives such as first and second, and the like may be used solely to distinguish one element or action from another element or action without necessarily requiring or implying any actual such relationship or order. Words such as "comprises" or "includes" are intended to define a non-exclusive inclusion, such that a method or apparatus that comprises a list of elements does not include only those elements but may include other elements not expressly listed, including elements that are inherent to such a method or apparatus.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

REFERENCES

1. Banerjee, S., et al., Gross trunnion failure after primary total hip arthroplasty. J Arthroplasty, 2015. 30(4): p. 641-8.
2. Lavernia, C. J., et al., Trunnion-Head Stresses in THA: Are Big Heads Trouble? J Arthroplasty, 2015. 30(6): p. 1085-8.
3. Pastides, P. S., et al., Trunnionosis: A pain in the neck. World J Orthop, 2013. 4(4): p. 161-6.
4. Porter, D. A., et al., Modern trunnions are more flexible: a mechanical analysis of THA taper designs. Clin Orthop Relat Res, 2014. 472(12): p. 3963-70.

The invention claimed is:

1. A device for redressing a tapered portion of an orthopaedic implant comprising:
   a grinding member adapted to matingly contact or engage at least a portion of the tapered portion;
   a housing adapted for removably receiving the grinding member therein, the housing having an opening at or towards a distal end to receive the tapered portion therethrough; and
   a connector at or towards a proximal end for operably connecting the housing to a drill member,
   wherein the housing further includes a cap disposed at or towards a distal end thereof, the cap comprising the opening and configured for reversibly closing the housing and retaining the grinding member therein.

2. The device of claim 1, wherein the grinding member comprises first and second portions that are separable from each other.

3. The device of claim 1, wherein the grinding member comprises a tapered aperture or recess to facilitate contact or engagement of the tapered portion with an inner grinding surface therein.

4. The device of claim 3, wherein the tapered aperture or recess is substantially frustoconical in shape.

5. The device of claim 1, wherein the housing comprises a recessed portion for removably receiving the grinding member therein.

6. The device of claim 5, wherein the recessed portion and the grinding member are substantially frustoconical in shape.

7. The device of claim 1, wherein the cap includes an annular lip disposed at or towards the distal end thereof and extends inwardly therefrom so as to define the opening of the housing therebetween.

8. The device of claim 3, wherein the housing includes one or more apertures that extend through an outer wall thereof into the recess.

9. The device of claim 8, wherein the housing includes first and second apertures disposed at opposing sides of the housing.

10. The device of claim 1, wherein the housing includes a cylindrical portion at the distal end and a tapered portion extending proximally from the cylindrical portion to the connector.

11. A kit comprising the device of claim 1 and a drill member.

12. A method of redressing a tapered portion of an orthopaedic implant including the steps of:

i. providing a device comprising: a grinding member adapted to matingly contact or engage at least a portion of the tapered portion; a housing adapted for removably receiving the grinding member therein, the housing having an opening at or towards a distal end to receive the tapered portion therethrough; a connector at or towards a proximal end for operably connecting the housing to a drill member; and a cap disposed at or towards a distal end thereof, the cap comprising the opening and configured for reversibly closing the housing and retaining the grinding member therein;

ii. contacting or engaging the device with the tapered portion; and iii. redressing the tapered portion with the device.

* * * * *